United States Patent
Hendricks et al.

(10) Patent No.: US 12,232,719 B2
(45) Date of Patent: Feb. 25, 2025

(54) IMPLANTABLE DEVICE

(71) Applicant: University Of Cape Town, Cape Town (ZA)

(72) Inventors: Mogamat Rushdie Hendricks, Cape Town (ZA); Deon Bezuidenhout, Cape Town (ZA)

(73) Assignee: University Of Cape Town, Cape Town (ZA)

( * ) Notice: Subject to any disclaimer, the term of this patent is extended or adjusted under 35 U.S.C. 154(b) by 0 days.

(21) Appl. No.: 18/676,156

(22) Filed: May 28, 2024

(65) Prior Publication Data

US 2024/0307051 A1 Sep. 19, 2024

Related U.S. Application Data

(63) Continuation of application No. 17/356,381, filed on Jun. 23, 2021, now Pat. No. 12,016,547, which is a
(Continued)

(30) Foreign Application Priority Data

Jun. 10, 2016 (GB) ..................................... 1610177

(51) Int. Cl.
*A61B 17/04* (2006.01)
*A61B 17/00* (2006.01)
(Continued)

(52) U.S. Cl.
CPC .... *A61B 17/0401* (2013.01); *A61B 17/06066* (2013.01); *A61B 17/06166* (2013.01);
(Continued)

(58) Field of Classification Search
CPC ...... A61B 17/0401; A61B 2017/00004; A61B 2017/00814; A61B 2017/0414;
(Continued)

(56) References Cited

U.S. PATENT DOCUMENTS 6,045,571 A   4/2000 Hill et al.
6,511,498 B1  1/2003 Fumex
(Continued)

FOREIGN PATENT DOCUMENTS

CA   2847581 A1   12/2006
EP   1506790 A1    2/2005
(Continued)

OTHER PUBLICATIONS

Office Action Dated Feb. 22, 2021 in Chinese Appicatlion No. 201780042741.8, 8 pages.
(Continued)

*Primary Examiner* — Julian W Woo

(74) *Attorney, Agent, or Firm* — Lee & Hayes, P.C.

(57) ABSTRACT

An implantable device for aiding in generating connective tissue between a pair of anatomical structures in a mammalian body is provided. The device includes an elongate, flexible tether which can be secured between the anatomical structures and which carries a scaffold which is generally porous so as to be capable of promoting tissue ingrowth and collagen deposition along its length. The scaffold extends along the tether for a sufficient distance so that it is securable in at least close proximity to an anatomical structure at either end. The pores in the scaffold extend through the scaffold and each has a diameter in the range of about 10 μm to about 200 μm. The length of the tether is selected to be a desirable maximum distance between the anatomical structures along a desired path when secured therebetween.

13 Claims, 9 Drawing Sheets

Related U.S. Application Data continuation of application No. 16/308,429, filed as application No. PCT/IB2017/053421 on Jun. 9, 2017, now abandoned.

(51) Int. Cl.
*A61B 17/06* (2006.01)
*A61B 17/24* (2006.01)

(52) U.S. Cl.
CPC .... *A61B 17/24* (2013.01); *A61B 2017/00004* (2013.01); *A61B 2017/00814* (2013.01); *A61B 2017/0414* (2013.01); *A61B 2017/044* (2013.01); *A61B 2017/0464* (2013.01); *A61B 2017/0619* (2013.01); *A61B 2017/248* (2013.01)

(58) Field of Classification Search
CPC ...... A61B 2017/044; A61B 2017/0464; A61B 2017/0619
See application file for complete search history.

(56) References Cited

U.S. PATENT DOCUMENTS

| | | | |
|---|---|---|---|
| 7,582,105 | B2 | 9/2009 | Kolster |
| 7,594,921 | B2 | 9/2009 | Browning |
| 7,975,700 | B2 | 7/2011 | Frazier |
| 7,981,023 | B2 | 7/2011 | Nowlin et al. |
| 8,096,303 | B2 | 1/2012 | Dineen |
| 8,757,163 | B2 | 6/2014 | Dineen |
| 9,393,067 | B2 | 7/2016 | Van Der Burg |
| 9,408,742 | B2 | 8/2016 | Dineen et al. |
| 9,833,353 | B2 * | 12/2017 | Witt ................ A61B 17/0401 |
| 10,004,631 | B2 | 6/2018 | Wortelboer |
| 11,026,830 | B2 | 6/2021 | Wortelboer |
| 2002/0058959 | A1 | 5/2002 | Gellman |
| 2002/0183858 | A1 | 12/2002 | Contiliano et al. |
| 2007/0142698 | A1 | 6/2007 | Bourne et al. |
| 2007/0233276 | A1 | 10/2007 | Conrad |
| 2008/0066769 | A1 | 3/2008 | Dineen et al. |
| 2009/0007922 | A1 | 1/2009 | Harrington |
| 2009/0018655 | A1 | 1/2009 | Brunelle et al. |
| 2009/0044814 | A1 | 2/2009 | Iancea et al. |
| 2011/0021868 | A1 | 1/2011 | Browning |
| 2012/0289990 | A1 | 11/2012 | Karabey et al. |
| 2013/0006283 | A1 | 1/2013 | Carrison et al. |
| 2018/0092736 | A1 | 4/2018 | Lee et al. |
| 2020/0305859 | A1 | 10/2020 | Hendricks et al. |
| 2021/0330316 | A1 | 10/2021 | Hendricks et al. |

FOREIGN PATENT DOCUMENTS

| | | |
|---|---|---|
| EP | 2381904 A1 | 11/2011 |
| EP | 2623072 | 8/2013 |

OTHER PUBLICATIONS

Office Action for U.S. Appl. No. 17/356,381, mailed on Apr. 11, 2023, Mogamat Hendricks, "Implantable Device", 11 pages.

Office Action Dated Dec. 28, 2020 in U.S. Appl. No. 16/308,429, 17 pages.

Office Action for U.S. Appl. No. 17/356,381, mailed on Sep. 7, 2023, Hendricks, "Implantable Device", 9 pages.

Search Report Dated Aug. 29, 2017 in PCT/IB2017/053421, 4 pages.

Hamans, et al., "A novel tongue implant for tongue advancement for obstructive sleep apnea: feasibility, safety and histology in a canine model," Dec. 29, 2009, 12 pages.

Hamans, et al., "Handler tongue suspension," <<https://www.researchgate.net/publication/257867523>>, Oct. 2013, 9 pages.

* cited by examiner

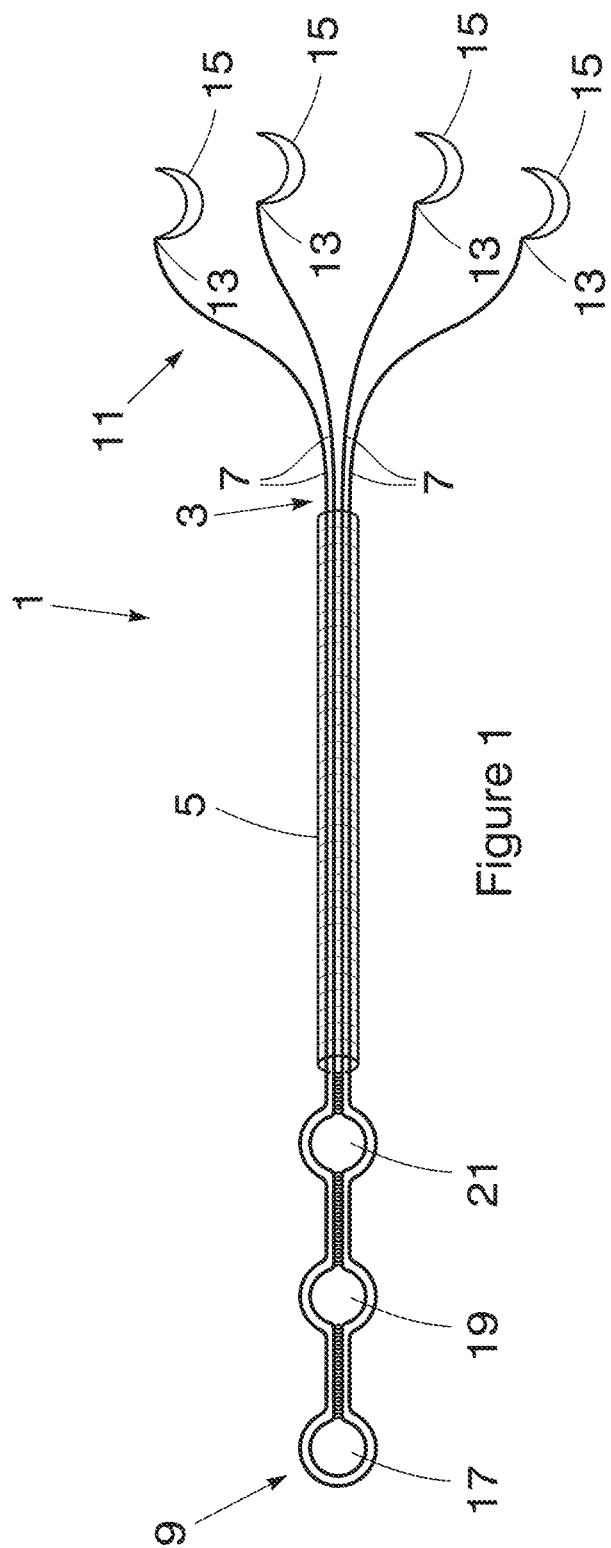
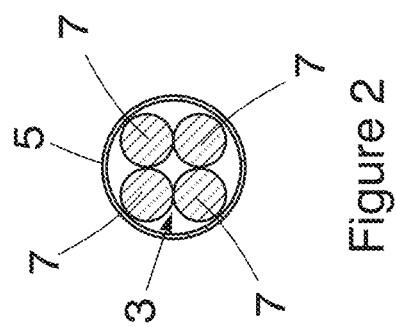

IMPLANTABLE DEVICE

CROSS-REFERENCE TO RELATED APPLICATIONS

This application is a continuation of U.S. patent application Ser. No. 17/356,381, filed Jun. 23, 2021, which is a continuation of U.S. patent application Ser. No. 16/308,429, filed on Dec. 7, 2018, which is a U.S. National Phase Patent Application of International Patent Application No. PCT/IB2017/053421, filed Jun. 9, 2017, which claims priority to Great Britain Patent Application No. 1610177.6 filed Jun. 10, 2016, the entire contents of each of which are incorporated by reference herein.

FIELD OF THE INVENTION

This invention relates to an implantable device and method for using such a device. One aspect of the invention provides for an implantable device which may be useful in the treatment of conditions relating to sleep apnoea.

BACKGROUND TO THE INVENTION

Obstructive sleep apnoea (OSA) is a serious, debilitating condition characterised by blockage of the upper airway during sleep as a result of collapse of the soft tissues in the throat. OSA is associated with significant morbidity and mortality, the impact of which has not as yet been fully defined and assessed in the global community. It is estimated that approximately 2% to 4% of the adult population in Western countries are affected, but these figures may represent a gross under-estimation of the problem. Patients suffering from OSA have sleep fragmentation and deprivation as they are unable to achieve adequate rapid eye movement sleep resulting in a non-refreshing sleep pattern. The major symptom of OSA is excessive daytime sleepiness (EDS). As a result, lack of concentration and memory, changes in mood and personality as well as an increase in workplace and traffic accidents have been linked to EDS. Moreover, there are significant comorbidities linked to OSA. These include cardiovascular, cerebrovascular, endocrine/metabolic complications and premature death.

There exists a strong relationship between obesity and OSA. It has been reported that 60-90% of patients suffering from OSA have a body mass index (BMI)≥30 Kg/m$^2$. In 1997, the World Health Organization formally recognized the global nature of obesity and declared it an epidemic. As the prevalence of obesity increases there is likely to be a parallel increase in OSA. In the adult population, the prevalence of OSA is estimated at 25%, rising to 45% in obese individuals. While OSA is more common in men and in the elderly age group, it can also occur in children and young adults. Obesity in children and young adults is reaching epidemic proportions. Obese children have a 46% prevalence of OSA compared to children seen in a general paediatric clinic (33%). The risk of children and adolescents with OSA to develop metabolic syndrome is six fold greater than their counterparts without OSA. Obesity is considered a major risk factor in the development and progression of OSA. In obese and severely obese individuals, the prevalence of OSA is nearly twice that of normal BMI adults. Moreover, a 10% weight gain in patients with mild OSA can increase their risk by 6 times to progress to severe OSA while an equivalent weight loss can result in a 20% improvement of OSA severity.

The upper airway in humans is the space between the nasal cavity and the larynx. Within this space lies the pharynx which is germane to airflow into the lungs and where the collapse takes place. The pharynx has three anatomical levels. The nasopharynx begins at the back of the nasal cavity and forms the uppermost portion of the pharynx. The oropharynx is the intermediate portion which contains the soft palate, uvula, base of tongue and epiglottis. Due to the high presence of soft tissue structures in the oropharynx it is the most likely anatomical part to obstruct and collapse. The hypopharynx is the area behind and below the opening of the larynx and extends into the oesophagus.

It is well known that the soft palate and tongue are both flexible structures with the soft palate providing a barrier between the nasal cavity and the mouth. In OSA the soft palate often hangs down between the tongue base and posterior pharyngeal wall. During sleep most muscles of the body relax while those of the respiratory system remain active. In particular, the diaphragm contracts and pushes the abdominal contents downwards in order to create a negative pressure within the chest cage. Air is thus sucked in through the nasal and oral cavities into the lungs through the pharynx. The negative pressure of inhalation is usually counteracted by the compliance of the pharyngeal wall. In patients with OSA the soft palate, tongue and/or epiglottis collapse against the posterior pharyngeal wall and block airflow into the trachea. As the airway becomes narrow turbulence in the pharynx causes the soft palate to vibrate thereby generating the sound of snoring.

It is possible that due to the deposition of fat at specific anatomic sites, as seen in obese patients, OSA may be aggravated. Compliance of the upper airway is negatively affected by the external pressure of para-pharyngeal fat deposition. This results in a smaller lumen and increased collapsibility of the pharynx, in so doing predisposing the individual to OSA. In addition, deposits of fat around the thorax (truncal obesity) can reduce chest compliance and functional residual capacity, thereby increasing oxygen demand. Visceral obesity is also commonly seen in OSA.

The consistency of the effect of body weight on the progression of the disease process across different cohorts strongly suggests that many patients with OSA present with a clinical history of recent weight gain. In view of the above and given the fact that obesity is reaching epidemic proportions, the close association between weight gain and disease progression heightens the concern that OSA, with its attendant plethora of serious comorbidities, as well as attendant complications, will inevitably impose an enormous financial burden upon health care delivery.

The basic epidemiological features of OSA are well established. The diagnosis of OSA is dependent upon both subjective and objective appraisal. A comprehensive clinical and sleep history includes the evaluation of subjective symptoms such as habitual snoring, EDS, nocturnal witnessed apnoea and a physical examination. The gold standard for the objective measurement of sleep disordered breathing (SDB) remains the polysomnogram (PSG) or sleep study. During sleep, it is often the case that brief obstructions of airflow and/or small decreases in the amount of airflow into the lungs can occur. An obstruction of airflow for more than 10 seconds is referred to as an apnoea.

OSA is defined by the number of apnoea and hypopnoea episodes per hour of sleep (apnoea-hypopnoea index, AHI) reflecting the departure from the normal physiology of breathing during sleep. Apnoeas are further classified as obstructive, central, or mixed based on whether effort to breathe is present during the event. A hypopnoea is defined as a reduction in airflow that is followed by an arousal from sleep or a decrease in oxyhaemoglobin saturation. Commonly used definitions of a hypopnoea require a 25% or 50% reduction in oronasal airflow associated with either a reduction in oxyhaemoglobin saturation or an arousal from sleep. The term "OSA syndrome" is used to indicate a clinical entity defined by an elevated AHI (having 10 or more episodes of apnoea or hypopnea per hour of sleep) in conjunction with hypersomnolence or related problems in daytime function and is synonymous with the term "obstructive sleep apnoea-hypopnoea syndrome"(OSAHS).

CPAP or continuous positive airway pressure treatment remains the gold standard for OSA because of its effectiveness in the elimination of apnoea and improvements in its sequalae. It operates by delivering air into the patient's airway through a specifically designed nasal mask or pillow. The inflow of air creates a positive pressure during inhalation, thereby maintaining an open airway and pushing and splinting the tongue base in a forward direction. In this way compliance and patency is maintained. Outcomes of randomised trials have shown substantial improvements in both sleepiness and neurocognitive performance of patients on nasal CPAP compared with those on placebo or sub therapeutic CPAP. Moreover, improvements in blood pressure have been shown with CPAP treatment. However, CPAP adherence is still difficult. Patency of the upper airway is germane to comfort and successful application, and thus demands the use of heated humidification, nasal decongestants and steroids as well as intensive support with regular follow-up to improve CPAP adherence. Besides compliance, the CPAP apparatus presents local problems such as bloating, nasal drying, dry eyes and itchiness of facial skin. In addition, bed partners are adversely affected. CPAP is also dependent upon electrical power making it difficult to use while travelling. As a result, CPAP compliance is only about 40%. Also, the high cost of CPAP delivery makes it a problem in third world countries and the routine use of such devices is difficult to justify.

Surgical treatments have also been advocated for the treatment of OSA. The most common surgical procedure for OSA is uvulopalatopharyngoplasty (UPPP) in which the uvula and redundant soft tissue of the soft palate is resected. The long term success of UPPP is only 20% after 2 years. Only about 41% of patients who undergo the procedure obtain an AHI of fewer than 20 events per hour. In addition, 20 events per hour is not always judged an adequate surgical outcome, especially in view of the uncertain correlation between AHI and apnoea complications. In many cases, snoring will stop after UPPP, but disordered breathing continues, leading to silent apnoea. Thus, the role of UPPP without tongue base advancement surgery for treatment of OSA is rather limited.

Radiofrequency (RF) treatment of the tongue base produced promising early results but was not consistent in the long term. Newer surgical approaches, such as laser-assisted palatal procedures and radiofrequency ablation techniques, have also been disappointing.

Surgical implants have also been used to treat OSA. The AIRvance system made by Medtronic uses a titanium screw that is inserted into the posterior aspect of the mandible at the floor of the mouth. A loop of suture is passed through the base of the tongue and attached to the screw. This procedure provides a hammock or suspension for the tongue, making it less likely for the base of the tongue to collapse during sleep. However, during wakefulness, the suture material acts as a cutting device and migrates anteriorly losing its efficacy within a few months.

Another tongue suspension device known as the Repose™ also has only limited efficacy. This device also utilises the suture and screw concept. However, the gains appear to be only short term and its long term prognosis as a tongue suspension device is poor.

US2008/066769A1 (Dineen) also discloses a flexible elongate element which is secured between the mandible and the base of the tongue. A tensioner is provided by Dineen which assists in adjusting the tension in the elongate element after implantation. This device is complex and considered to have the same limitation as those of the AIRvance and Repose™ devices. Dineen discloses coating the elongate element with a bioabsorbable coating which may cause scar or connective tissue formation about the elongate element and which is thought may help tightening the tongue tissue to resist migration of the implant. The connective tissue is intended to be formed at the base of the tongue only. It is aimed at preventing muscle tearing or damage caused by the implant of barbs or hooks. However, any scar or connective tissue formed on the coating about the elongate element will at best form a sheath over the elongate element and its movement will of course be limited to that of the elongate element. Furthermore, the device disclosed in Dineen is mostly non-absorbable and consequently may be more prone to infection which may limit its clinical application.

While tongue advancement offers a useful method of treating OSA, there is currently no practical, long term method of achieving this.

SUMMARY OF THE INVENTION

In accordance with this invention there is provided an implantable device for aiding in generating connective tissue between a pair of anatomical structures in a mammalian body including an elongate, flexible tether which can be secured between the anatomical structures and which carries a scaffold which is generally porous so as to be capable of promoting tissue ingrowth and collagen deposition along its length, the scaffold extending along the tether for a sufficient distance so that it is securable in at least close proximity to an anatomical structure at either end, and wherein the length of the tether is selected to be a desirable maximum distance between the anatomical structures along a desired path when secured therebetween, characterised in that the pores extend through the scaffold and each have a diameter in the range of about 10 μm to about 200 μm.

Further features of the invention provide for the pores to extend through the scaffold; each pore to have a diameter of about 50 μm to 180 μm, more preferably 100 μm to 150 μm, most preferably about 150 μm; for the scaffold to be sleeve-like and to extend over the tether; for the scaffold to be tubular; for the scaffold to be made from a polymeric material and to be formed by a moulding, casting or melt blending/extrusion process, with or without the addition and extraction of porogens; and for the scaffold to be made from micro- or nanofibers.

Yet a further feature of the invention provides for the scaffold to be capable of at least some elastic elongation.

Still further features of the invention provide for the scaffold to be manufactured from a stable or non-degradable material; for the stable or non-degradable material to be a thermoplastic elastomer; for the thermoplastic elastomer to be selected from: polyurethanes such as Pellethane™, Estane™, Texin™, elastane and CarboSil™; polyurethane ureas such as Biomer™, Biospan™, Mitrathane™ and Lycra™; carbonate containing polyurethanes such as Chronoflex™ and Bionate™; polydimethylsiloxane containing polyurethanes or polyurethane ureas such as Pursil™, ElastEon™ and Cardiothane™; polyurethanes containing both carbonate and polydimethylsiloxane moieties; polyurethanes containing soft segments such as hydrocarbons or dimerol and/or partial crosslinking for improved chemical stability and mechanical properties; silicone, Silastic™, Silupran™, styrene, (co)polyester, polyolefin, polydiene and polyvinyl chloride based synthetic elastomers; or a natural rubber; for the elastomer to preferably be CarboSil™ or one of the polyurethane ureas.

Alternatively, for the scaffold to be manufactured from an absorbable material; for the absorbable material to be selected from polylactic acid, polyglycolic acid, polycaprolactone, polydioxanone, polyhydroxybuterate, polyiminocarbonates, polysebacic acid, degradable polyurethanes such as DegraPol™ and copolymers thereof.

Yet further features of the invention provide for the tether to be absorbable; for the tether to be provided by a plurality of filaments; for the filaments to be made from suture material; and for the filaments to be welded, woven or braided together along part of their length.

Still further features of the invention provide for each end of tether to be securable to an anatomical structure through one or more loops in the tether, or a suturing needle secured to the end of each filament, or a combination of these; for the or each loop to be shaped to receive a fixation screw; for the one or more loops to be equally spaced along the length of the tether; and for the loops to be spaced approximately 10 mm apart.

According to one aspect of the invention the device is configured to provide support for a tongue base, the scaffold being selected to be between 50 mm and 100 mm long, preferably about 70 mm long; for the scaffold to be about 0.5 mm thick and have an internal diameter of about 2 mm and for the tether to be made from two or more, preferably four, filaments, and wherein the filaments are shaped to provide one or more loops at one end and each have a suturing needle secured to the opposite end.

Further features according to this aspect provide for the one or each loop to be shaped to receive bone fixation screw; for there to be three loops spaced along the length of the tether, preferably spaced apart by about 10 mm.

The invention also provides an implantable device which is suitable for aiding in generating connective tissue between the base of a tongue and a chin in a mammalian body and shaped to be securable at its ends between the base of a tongue and a chin, the device including an elongate and flexible tether with a tensile strength sufficient to advance the base of the tongue towards the chin and maintain it in such position, and characterised in that the tether is made of an absorbable material and in that a sleeve-like scaffold which is generally porous so as to be capable of promoting tissue ingrowth and collagen deposition along its length is provided over the tether, the scaffold extending along the tether for a sufficient distance so that it is securable in at least close proximity to the base of the tongue and chin at either end.

Further features of the invention provide for the scaffold to be made from a polymeric material and for the pores to extend through the scaffold and each have a diameter in the range of about 10 μm to 200 μm, preferably about 50 μm to 180 μm, more preferably 100 μm to 150 μm, most preferably about 150 μm.

Still further features of the invention provide for the tether to be provided by a plurality of filaments; for the filaments to be made of suture material; for the filaments to be shaped to provide one or more loops at one end of the tether; for a suturing needle to be secured to each filament at the opposite end of the tether; and for the or each loop to be shaped to receive fixation screws.

Still further features of the invention provide for the one or more loops to be equally spaced along the length of the tether; and for the loops to be spaced approximately 10 mm.

Yet further features of the invention provide for the scaffold to be between 50 mm and 100 mm long; for the scaffold to be about 0.5 mm thick; and for the scaffold to have an internal diameter of about 2 mm.

The invention also provides a method of generating connective tissue in a mammalian body which includes creating an incision in the body and securing between a pair of anatomical structures which are movable relative to each other an elongate, flexible tether carrying a scaffold such that the length of the tether is a desirable maximum distance between the anatomical structures along a desired path and wherein the scaffold is elongate and generally porous so as to be capable of promoting tissue ingrowth and collagen deposition along its length and secured such that it is in at least close proximity to the anatomical structures at either end and permitting tissue ingrowth and collagen deposition in and on the scaffold over a period of time.

A further feature of the invention provides for the pores to extend through the scaffold and each have a diameter in the range of about 10 μm to 200 μm, preferably about 50 μm to 180 μm, more preferably about 100 μm to 150 μm, alternatively about 125 μm to 180 μm, most preferably about 150 μm.

Further features of the invention provide for the tether to be made of a material which is absorbed into the body over a period of time; and for the scaffold to be made of a material which is stable and non-degradable or of a material that is absorbable and absorbed into the body over a period of time.

Still further features of the invention provide for the scaffold to be carried as a sleeve over the tether; and for the sleeve to be about 0.5 mm thick and have an internal diameter of about 2 mm.

The invention still further provides a method of providing a support for a tongue base which includes causing connective tissue to be generated between the base of the tongue and the chin by securing between the base of the tongue and the chin an elongate, flexible tether carrying an elongate sleevelike scaffold which is generally porous so as to be capable of promoting tissue ingrowth and collagen deposition along its length, advancing the base of the tongue towards the chin a desired distance using the tether, and permitting a tendon to be formed between the chin and tongue in and on the scaffold.

Further features of the invention provide for the tether to be made of an absorbable material and for the method to include the steps of stitching the device to the base of the tongue; and for providing one or more holes and screws for screwing the device into the chin.

The invention still further provides a method of treating sleep apnoea which includes securing between the base of the tongue and the chin an elongate, flexible tether carrying an elongate scaffold which is generally porous so as to be capable of promoting tissue ingrowth and collagen deposition along its length, advancing the base of the tongue towards the chin a desired distance using the tether, and permitting a tendon to be formed between the chin and tongue in and on the scaffold.

An embodiment of the invention will now be described, by way of example only, with reference to the accompanying drawings.

BRIEF DESCRIPTION OF THE DRAWINGS

In the Drawings:

FIG. 1 is a three-dimensional view of an implantable device for aiding in generating connective tissue in accordance with the invention;

FIG. 2 is a cross-section of the implantable device of FIG. 1;

FIGS. 8 to 17 are illustrations of the steps for implanting the implantable device into the tongue and chin.

DETAILED DESCRIPTION WITH REFERENCE TO THE DRAWINGS

Figure 3:
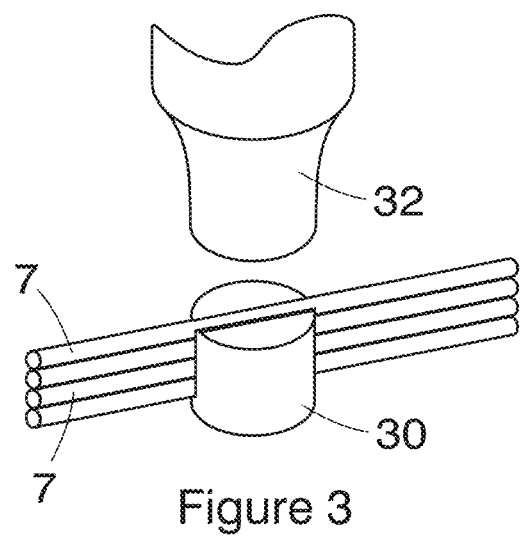
FIG. 3 is a schematic illustration showing tethers stacked in a welding nest prior to being contacted with an ultrasonic horn for ultrasonic welding of the tethers.

An implantable device is provided which may be used to aid in generating connective tissue between a pair of anatomical structures in a mammalian body. The connective tissue is formed by collagen and other tissues and depending on the nature of the anatomical structures the connective tissue may be termed a tendon or a ligament. A tendon extends between a muscle and a bone while a ligament extends between bones or cartilages at a joint or supporting an organ.

It is anticipated that the device will typically be used to aid in generating connective tissue between anatomical structures which are movable relative to each other but it could be employed where the structures are generally stationary relative to each other.

The device includes an elongate, flexible tether which can be secured between the anatomical structures and which carries a scaffold. The length of the tether is selected to be a desirable maximum distance between the anatomical structures along a desired path when secured between tethers. For movable structures this distance would be the approximate desired distance when the structures are fully flexed or extended or moved away from each other. For stationary structures the distance would be the approximate desired distance the structures should be apart from each other.

The tether may also be selected to be capable of elastic elongation for certain applications. Where the tether is capable of elastic elongation its length may be selected to be a desirable maximum distance between the anatomical structures along a desired path when secured between tethers and when in an elastically elongated condition. This may assist in ensuring that a certain degree of slack in the tether is avoided, possibly completely avoided, when the anatomical structures are a minimum distance apart.

The tether is also selected to provide a desired amount of tensile strength which is generally the amount of strength required to overcome forces of separation exerted between the anatomical structures. This ensures that the structures do not move more than the desired distance apart from each other. Depending on the anatomical structures and the typical forces exerted between them the tether may be required to have a tensile strength of between 10 N and 1000 N.

Typically the tether can be made from suture material, but any suitable biocompatible material could be used. In this specification, the term "suture material" shall have its widest meaning and include any biocompatible material from which an elongate thread with sufficient tensile strength to provide mechanical support to anatomical structures can be formed. Suture materials can be natural or synthetic, absorbable or non-absorbable and can have a range of different characteristics such as being pliable, elastic or flexible. The term "absorbable" as used herein shall have its widest meaning and generally refers to the ability of a material to be degraded in the body so as to lose its structural integrity over time. Alternative terms that may be used to describe this characteristic of a material include degradable, reservable and bioresorbable.

Commonly used suture material offers the advantage of being readily available and its properties well understood. The tethers can be made of absorbable suture materials such as polylactic acid, polyglycolic acid, polycaprolactone, copolymers of the aforementioned, polydioxanone (PDO/PDS), polyhydroxybuterate, polyiminocarbonates, polysebacic acid copolymers, copolymers of lactide and glycolide such as polyglactin (Vicryl™), homo polymers of glycolide such as Dexon™ (polyglyconic acid), polyglyconate (Maxon™) or poliglecaprone (Monocryl™). The tethers are preferably made of polydioxanone (PDO) or polyglactin (Vicryl™) which have the required long term strength whilst also being biodegradable. Polydioxone (PDO) has been found to work well and it is degraded within the body over a period of time through the process of hydrolysis.

Alternatively, the tethers can be made of non-degradable or stable materials such as polyethylene, ultra-high molecular weight polyethylene, polypropylene, polyamides (Kevlar™), nylons, polyesters, or other high strength fibre forming polymers. In the event that non-degradable tethers form part of the device, it is foreseen that the tethers may be removed a certain period of time after implantation of the device and following the generation of connective tissue between the anatomical structures. If the tether is to be removed it will preferably be configured so that it can be removed with the least amount of difficulty or damage to the surrounding tissue. Thus, the tether may, for example, be formed with a generally uniform, smooth surface to facilitate it being pulled or withdrawn from surrounding connective tissue.

The tether may be provided by a number of filaments, each of which can be provided by suture material, and the filaments can also be worked to have a desired tensile strength. For example the filaments can be folded, braided or woven into a suitably strong configuration. They can also be bonded together, for example by ultrasonic welding, compression thermal welding, RF welding or shrink tube welding, or alternatively may be bonded together using chemical, solvent or adhesive based techniques.

The tether could also be made from a suitable material to have a desired thickness or cross-sectional profile, and could have grooves or channels in its surface if desired. The tether need not be solid but may have a braided, twisted or otherwise non-uniform surface and may also be porous or so as to permit the migration of cells into the tether structure.

The tether can be secured in position by any suitable means depending on the nature of the anatomical structures. Where secured to muscle it could be passed through the muscle and knotted in position. Conveniently, a suturing needle may be secured to the end of the tether or each filament making up the tether to assist in passing it through the muscle and knotting it in position. Where secured to bone it could be secured to a screw placed in the bone. If secured between two bones or bony structures it could be secured by a screw at each end. The screws can conveniently extend through loops formed in the tether. Where it is secured to a screw or similar device placed in bone it is desirable that the screw also be a made from an absorbable material. One example of such material is Lactosorb™ (Biomet).

The tether defines a path for growth of connective tissue which is initiated by cellular migration into the scaffold. The porous scaffold is selected to permit and encourage the ingrowth of fibrovascular tissue from surrounding tissue along its length. Cellular migration refers to the migration of cells such as fibroblasts and myofibroblasts into the pores of the scaffold. These cells deposit extracellular matrix, including collagen in and on the scaffold and eventually connective tissue is generated. The scaffold is provided by a porous body, preferably a membrane, in which the pores each have a diameter in the range of about 10 µm to 200 µm, preferably about 50 µm to 180 µm, more preferably 100 µm to 150 µm, most preferably about 150 µm. A 10% to 15% coefficient of variation (CV) is typically expected for the pore sizes. The pores need not have a uniform diameter but it is desirable in the case of non-uniform diameters that the minimum and maximum diameters fall within these ranges. The pores extend through the body to permit fibrovascular material to propagate through the scaffold. As the pores extend from one side to the other of the scaffold material fibrovascular material is able to propagate from the outside of the scaffold through to the inside of the scaffold which abuts or is in proximity with the tether. This culminates in the deposition of collagen and subsequently orderly connective tissue is established and propagated on both sides of the body of the scaffold.

The scaffold is made from a biocompatible material, preferably a thermoplastic elastomer such as a polyurethane, even more preferably CarboSil™ with a hardness (Durometer hardness Shore A) of 80A.

Other suitable elastomeric materials that the scaffold may be made of which are stable, i.e. non-degradable, include polyurethanes such as Pellethane™, Estane™, Texin™ and elastane; polyurethane ureas such as Biomer™, Biospan™, Mitrathane™ and Lycra™; carbonate containing polyurethanes such as Chronoflex™ and Bionate™; polydimethylsiloxane containing polyurethanes or polyurethane ureas such as Pursil™, Elast-Eon™ and Cardiothane™; polyurethanes containing both carbonate and polydimethylsiloxane moieties; polyurethanes containing soft segments such as hydrocarbons or dimerol and/or partial crosslinking for improved chemical stability and mechanical properties; silicone, Silastic™, Silupran™, styrene, (co)polyester, polyolefin, polydiene and polyvinyl chloride based synthetic elastomers; or a natural rubber.

Alternatively, the material could be an absorbable material that is absorbed into the body over a period of time such as polylactic acid, polyglycolic acid, or polycaprolactone, copolymers of the three aforementioned materials, polydioxanone, polyhydroxybuterate, polyiminocarbonates, polysebacic acid copolymers, and degradable polyurethanes, such as DegraPol™.

Any suitable method of making the scaffold can be used. For example it could be made by a moulding, casting or melt blending/extrusion process, with or without the addition and extraction of porogens. Porogens are particles of a specified shape and size that are used to make pores in structures made by any one or more of the above processes. The porogens are usually dissolved away after the material has set thereby providing a microporous material. While porogens often take the shape of beads they could also be provided by nano- or microfibers which can be dissolved or otherwise removed from the structure to provide pores. Further alternative methods of making the scaffold involve the use of micro- or nanofibers which form a porous mat or pile, such as by spinning onto a flat surface, or which are formed into a thread and then woven or knitted or braided into a suitable shape, or by directly spinning tubular structures onto a rotating mandrel using the process of electrospinning.

Where spherical porogens are used to create the pores these can be sized used appropriate sieves. Typical sieves may be in the ranges 30-45 µm, 53-63 µm, 63-75 µm, 90-106 µm and 150-180 µm, each with an approximate CV of 10% to 15%.

The material used for the scaffold may be made in the form of a membrane which may have a thickness of less than 2 mm, preferably less than 1 mm, most preferably about 0.5 mm.

The scaffold can be carried on the tether in any suitable fashion. Conveniently it could have a tubular shape which extends over the tether as a sleeve or in a sleeve-like manner. The tubular scaffold may be formed from a single tubular member or a series of rings or squat tubes that are stacked or attached to one another to form an elongate tubular structure.

The internal diameter or circumference of the scaffold should be complementary to, or approximate, the outer diameter or circumference of the tether. It is not necessary for the scaffold to provide a very tight fit over the tether although it should not be too loose either. It is desirable that a contiguous, or lightly touching, fit be provided. When the scaffold lightly touches the tether it allows some space to exist between the tether and scaffold to permit collagen deposition between the two. With the scaffold contiguous with the tether about its circumference cells are thus still able to migrate between the scaffold and tether. Where the tether is made of a number of strands or filaments of suture material it typically has a non-uniform external surface. A scaffold carried as a sleeve over such a tether may provide a stretch fit and leave sufficient space due to the non-uniform surface. Also, as the tether absorbs into the body, collagen and other tissue fills the entire space left by it.

The scaffold should be flexible. It should preferably also be capable of at least some elastic elongation particularly where the tether is capable of elastic elongation. Where the tether is not capable of significant elastic elongation this property is not strictly required of the scaffold.

The scaffold is preferably elongate and continuous but it will be understood that small gaps could be provided in its length or porosity which will be spanned by fibrovascular material. The length of the scaffold will typically approximate that of the tether between the anatomical structures so that the scaffold is held in close proximity, or abutting, the anatomical surfaces.

The scaffold need not have a tubular shape and could be shaped to partially cover the tether or be integrated into the tether, such as by weaving, braiding, making a yarn. Thus, for example, yarns of a suitable scaffold material could be twisted or woven together with the suture material of the tether.

While it is desirable to secure the ends of the scaffold abutting or in close proximity to the anatomical structures, it is not critical that this be done. Heterotopic bone formation will typically ensure that bone grows out and joins the collagen within and on the scaffold creating a truly biological attachment.

It is also desirable that movement of the device occur as this stimulates the growth and alignment of collagen. Importantly, it also stops ossification or the formation of bone from the tissue.

The cross-sectional shape of the device is generally dependant on the application and the type of connective tissue it is desired to generate. In many instances the tether and scaffold will have a generally round or circular cross-section but it is envisaged that a flattened, oval or strap-like profile could be used for approximating that of, for example, ligaments of long bones. This can be fairly easily achieved by, for example, braiding suture material into a strap-like configuration and sliding a complementary sleeve of scaffold material thereover in a sheath-like fashion.

In one application, an implantable device is provided that is suitable for aiding in generating connecting tissue between the base of a tongue and a chin in a mammalian body. The device is shaped to be securable at its ends between the base of the tongue and the chin. The device includes an elongate and flexible tether which has sufficient tensile strength along a length thereof to advance the base of the tongue towards to chin and maintain it in such position. A tensile strength required by the tongue to prevent it falling back against the throat may range between 10 N and 100 N, but is typically 30 N. The tether must therefore have a tensile strength that is at least 10 N, preferably at least 30 N. A tether with a tensile strength of between 10 N and 100 N should be sufficient. A generally porous scaffold is provided on the tether. The scaffold extends along the tether for a sufficient distance so that it is securable in close proximity to the base of the tongue and the chin to enable connective tissue to be generated between the base of the tongue and the chin. The implantable device which is configured to aid in generating connecting tissue between the base of a tongue and a chin is suitable for treating conditions related to sleep apnoea in humans.

One embodiment of an implantable device (1) is shown in FIGS. 1 and 2 and includes an elongate, flexible tether (3) which carries a scaffold (5). The tether (3) is provided by two round filaments (7) of suture material, in this embodiment polydioxanone (PDO) having a diameter grading of 0,0 USP, which are folded about themselves to provide first end (9), at which the filaments (7) are bent, and a second end (11) at which the ends (13) of the filaments (7) are loose.

A half-circle tapered needle (15) is attached to the end (13) of each filament (7). This may conveniently be achieved by crimping in conventional fashion.

Three loops (17, 19, 21) or eyelets are provided spaced apart from each other at the first end (9). The first loop (17) is provided at the end (9). The second loop (19) is spaced 10 mm from the first loop (17) and the third loop (21) spaced 10 mm from the second loop (19). Each loop (17, 19, 21) has an internal diameter of 2 mm in this embodiment.

Figure 4:
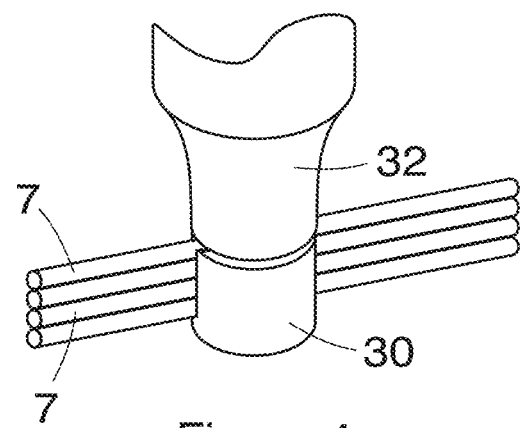
FIG. 4 is a schematic illustration showing how the tethers are bonded together when the ultrasonic horn is brought into contact with the welding nest.

The loops (17, 19, 21) are formed by bonding the filaments (7) together between the first loop (17) and second loop (19), the second loop (19) and third loop (21) and for about 10 mm after the third loop (21). In this embodiment the filaments (7) are bonded together using ultrasonic welding which may be achieved as follows. Referring to FIGS. 3 and 4, the four filaments (7) are placed within a welding nest (30) or anvil stacked one on top of the other. An ultrasonic horn (32) is then brought into contact with the welding nest (30) and used to apply vibrational energy to the stacked filaments (7). The abutting edges of the filaments serve as energy directors and the vibrational energy is transformed into frictional thermal energy which produces a localized weld without significant damage to the filaments (7).

Other bonding methods can be energy based or chemical, mechanical, solvent or adhesive based. For example, the filaments (7) could be subjected to other forms of welding energy including compression thermal welding with heated dies, RF welding to provide very local welding at the interface of the two fibers or shrink tube lap welding. While the first three methods of welding provide welded joints, the use of the shrink tube welding may be preferable as it produces a solid, seamless welded region.

Shrink tube welding uses a shrink tube that has a transition temperature (shrink temperature) that is greater than the melt temperature of the PDO filaments. Thus, as the shrink tube collapses or compresses at the transition temperature and exerts a compaction force on the filaments, the molten filament polymer flows together and effectively welds. The shrink tube is subsequently removed leaving the filaments in a welded state. Additionally, the shape of the welded zone may be adapted to preferred geometries of the loops (17, 19, 21) by a non-uniform shrink tube or by confinement of the shrink tube by horizontal compression.

Referring again to FIGS. 1 and 2, the scaffold (5) is, in this embodiment, provided by a membrane having a thickness of about 0.5 mm and which is tubular in shape with a length of about 70 mm and an internal diameter of about 2 mm. Importantly, the scaffold (5) is porous with the pores each having a diameter of about 125 μm to 180 μm and each extending through the membrane. In this embodiment the scaffold is made from a biocompatible polyurethane material called CarboSil™ from DSM.

The scaffold (5) is flexible and extends over the tether (3) in a sleeve-like manner. Conveniently, it can be inserted over the second end (11) of the tether (3) before the needles (15) are secured to the filaments (7). It provides a fairly loose fit over the tether (3) and space is thus provided between the filaments (7) and between the filaments and the scaffold (5). The scaffold (5) extends along the tether (3) for a sufficient distance so that it is securable in close proximity to the base of the tongue and the chin. The scaffold (5) serves as a platform for the growth of connective tissue and the growth and strengthening of the connective tissue is stimulated by the functioning and movement of the tongue as described in more detail above.

The scaffold (5) does not absorb in vivo, in this embodiment, but acts as a platform for the ingrowth of fibrocollagenous material. Its tensile strength is essentially increased with the deposition of orderly collagen fibers. The filaments (7) are absorbable in vivo and undergo degradation and absorption through hydrolysis over a period of 24 weeks. The filaments (7) are therefore expected to totally absorb within a period of 24 weeks, leaving the scaffold (5) filled with fibro-collagenous material, further strengthened by the tensile forces produced by physiological functioning of the intrinsic muscle.

The device (1) is suitable for aiding in generating connecting tissue specifically between the base of a tongue and a chin in a mammalian body. Such a device is shaped to be securable at its ends (9, 11) between the base of the tongue and the chin. The device includes an elongate and flexible tether (3) which has sufficient tensile strength along a length thereof to advance the base of the tongue towards to chin and maintain it in such position. A tensile strength required by the tongue to prevent it falling back against the throat may range between 10 N and 100 N, but is typically 30 N. The tether must therefore have a tensile strength that is at least 10 N, preferably at least 30 N. A tether with a tensile strength of between 10 N and 100 N may be suitable.

Figure 5:
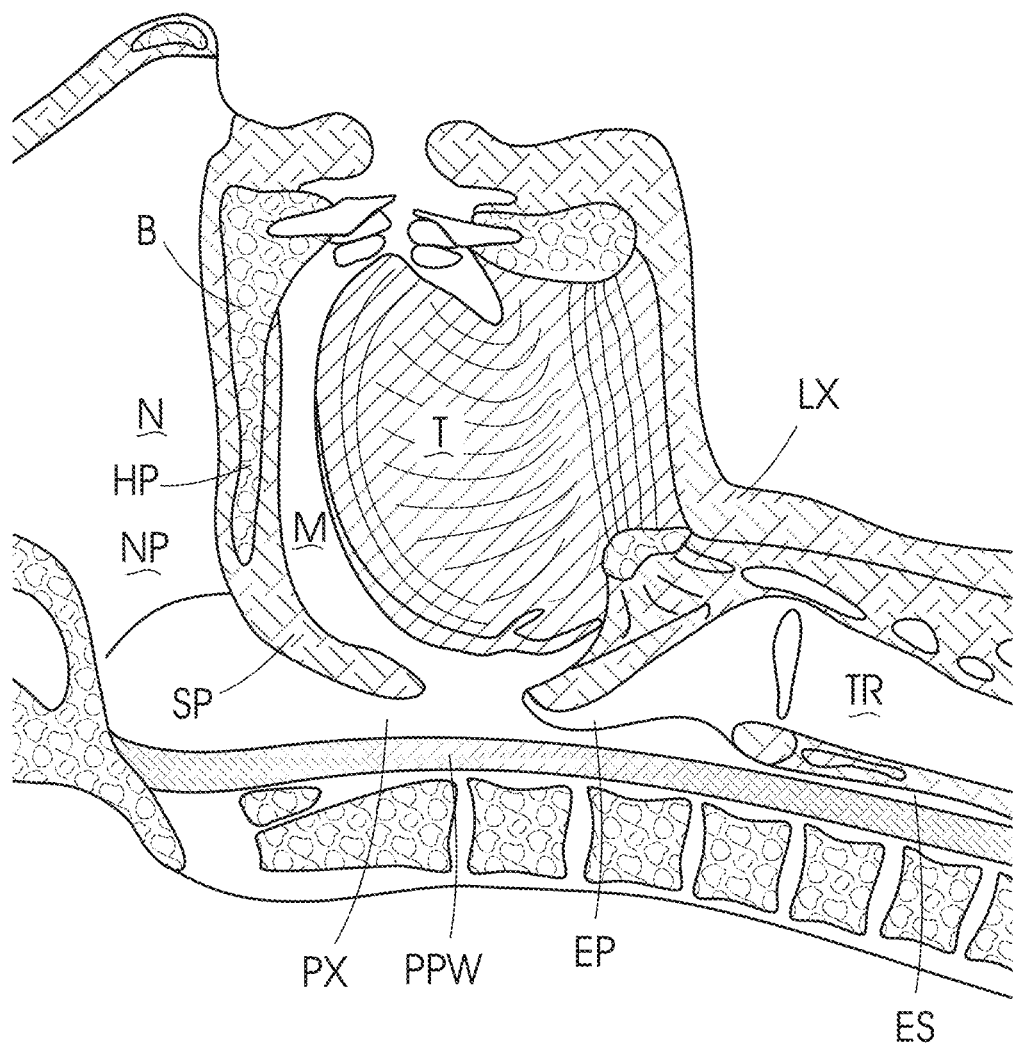
FIG. 5 is a cross-section of a human head showing anatomical structures.

Prior to describing the device (1) in use, the anatomy relevant to its use between the base of a tongue and a chin will be described. FIG. 5 shows a cross-section of a human head with anatomical structures including the nasal cavity N, bone B of the hard palate HP, the soft palate SP, the mouth M, the tongue T, the trachea TR, the epiglottis EP, the esophagus ES, and the posterior pharyngeal wall PPW. In the human head, an air filled space between the nasal cavity N and the larynx LX is referred to as the upper airway.

Figure 6:
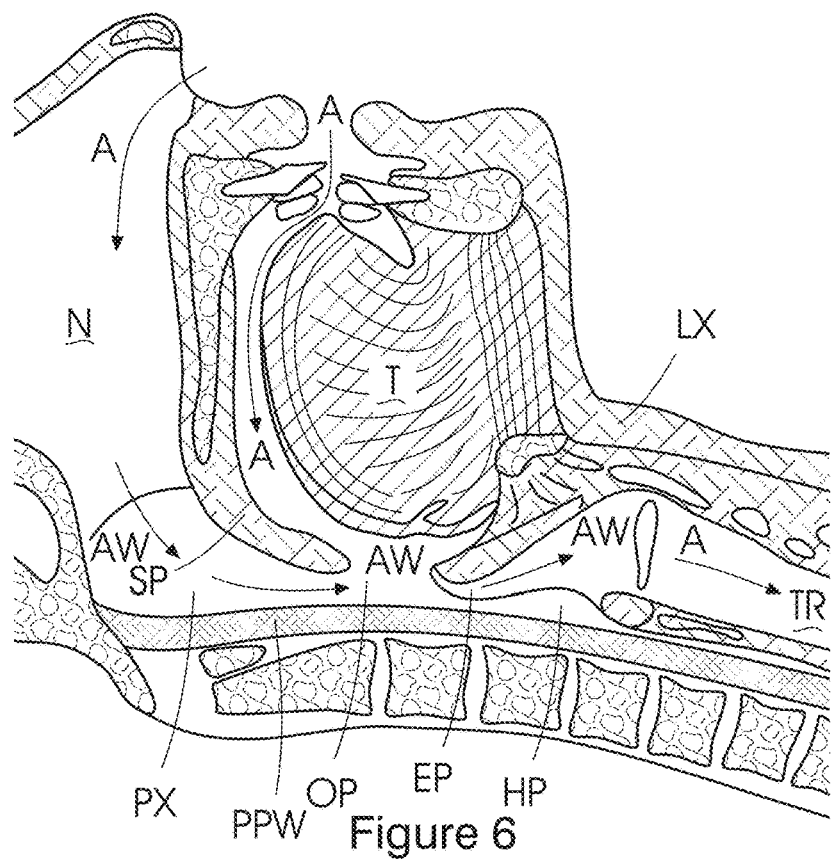
FIG. 6 is cross-section of a human head showing anatomical structures with arrows indicating the direction airflow into the trachea.

The most critical part of the upper airway associated with sleep disorders is the pharynx PX. Referring to FIG. 6, the pharynx has three different anatomical levels. The nasopharynx NP is the upper portion of the pharynx located in the back of the nasal cavity N. The oropharynx OP is the intermediate portion of the pharynx containing the soft palate SP, the epiglottis EP, and the curve at the back of the tongue T. The hypopharynx HP is the lower portion of the pharynx located below the soft tissue of the oropharynx OP. The oropharynx OP is the section of the pharynx that is most likely to collapse due to the high prevalence of soft tissue structure, which leaves less space for airflow. The hypopharynx HP lies below the aperture of the larynx and behind the larynx, and extends to the esophagus.

The soft palate and the tongue are both flexible structures. The soft palate SP provides a barrier between the nasal cavity N and the mouth. In many instances, the soft palate SP is longer than necessary and extends a significant distance between the back of the tongue T and the posterior pharyngeal wall PPW.

Figure 7:
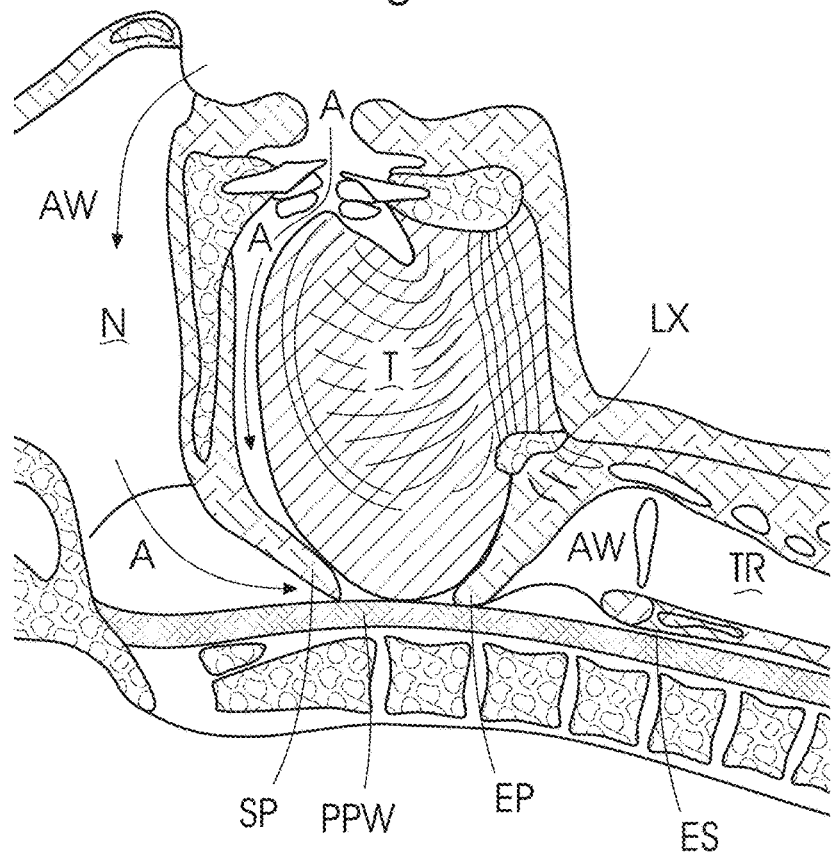
FIG. 7 is cross-section of a human head showing the anatomical structures when certain structures collapse to block airflow into the trachea.

Although the muscles relax throughout the body during sleep, most of the muscles of respiratory system remain active. During inhalation, the diaphragm contracts and causes negative pressure to draw air A into the nasal cavity N and the mouth M. The air then flows past the pharynx PX, through the trachea TR and into the lungs. The negative pressure causes the tissue of the upper airway to deform slightly, which narrows the airway AW passage. In apnoeic patients, the soft palate SP, the tongue T, and/or the epiglottis EP collapse against the posterior pharyngeal wall PPW to block airflow into the trachea, as shown in FIG. 7. As the airway AW narrows, airflow through the pharynx becomes turbulent which causes the soft palate SP to vibrate, generating a sound commonly known as snoring.

During sleep, humans typically experience brief obstructions of airflow and/or small decreases in the amount of airflow into the trachea and lungs. An obstruction of airflow for more than ten seconds is referred to as apnoea. A decrease in airflow by more than fifty percent is referred to as hypopnoea. The severity of sleep disorders is measured by the number of apnoeas and hypopnoeas that occur during every hour of sleep.

If apnoea or hypopnoea occurs more than five times per hour, most medical personnel diagnose the individual as having an upper airway resistance problem. Many of these patients often exhibit symptoms related to sleep disorders including sleepiness during the day, depression, and difficulty concentrating. Individuals having ten or more episodes of apnoea or hypopnoea during every hour of sleep are officially classified as having obstructive sleep apnea syndrome (OSAS). As the airway AW is obstructed, the individual makes repeated attempts to force inhalation. Many of these episodes are silent and are characterized by movements of the abdomen and chest wall as the individual strains to draw air into the lungs. Typically, episodes of apnoea may last a minute or more. During this time, oxygen levels in the blood will decrease. Ultimately, the obstruction may be overcome by the individual generating a loud snore or awakening with a choking feeling.

Referring to FIG. 6, when an individual is awake, the back of the tongue T and the soft palate SP maintain their shape and tone due to their respective internal muscles. As a result, the airway AW through the pharynx remains open and unobstructed. During sleep, however, the muscle tone decreases and the posterior surface of the tongue and the soft palate become more flexible and distensible.

Referring to FIG. 7, without normal muscle tone to keep their shape and anatomical position either alone or as a group, the posterior surface of the tongue T, the epiglottis EP, and the soft palate SP tend to easily collapse to block the airway AW.

The use of the implantable device (1) in the treatment of apnoea will now be described with reference to FIGS. 8 to 17 which illustrate the steps of implanting the device. The treatment includes providing a support for a tongue base by causing connective tissue to be generated between the base of the tongue and the chin by securing between the base of the tongue and the chin an elongate, flexible tether carrying an elongate scaffold which is generally porous so as to be capable of promoting tissue ingrowth and collagen deposition along its length, advancing the base of the tongue towards the chin a desired distance using the tether and permitting a tendon to be formed between the chin and tongue in and on the scaffold. After or during formation of the tendon the tether can be removed or be permitted to be absorbed into the body.

If the scaffold is tubular so as to be in the form of a sleeve, the formation of tendon on the scaffold includes tendon forming around and within the sleeve through cellular migration and connective tissue growth as discussed above. Such cellular migration and connective tissue growth also takes place in the pores of the scaffold. The scaffold need not have a tubular shape and could be shaped to partially cover the tether or be integrated into the tether, in which case the tendon forms on and around portions of the scaffold as well as in the pores of the scaffold.

Figure 8:
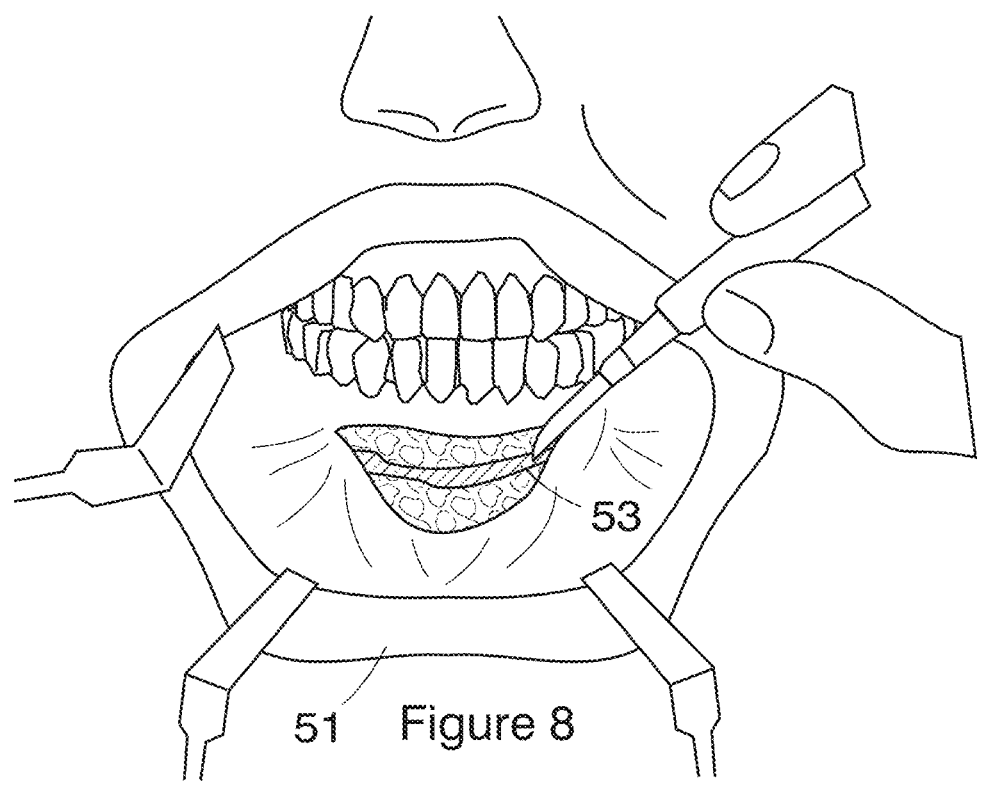
Figure 9:
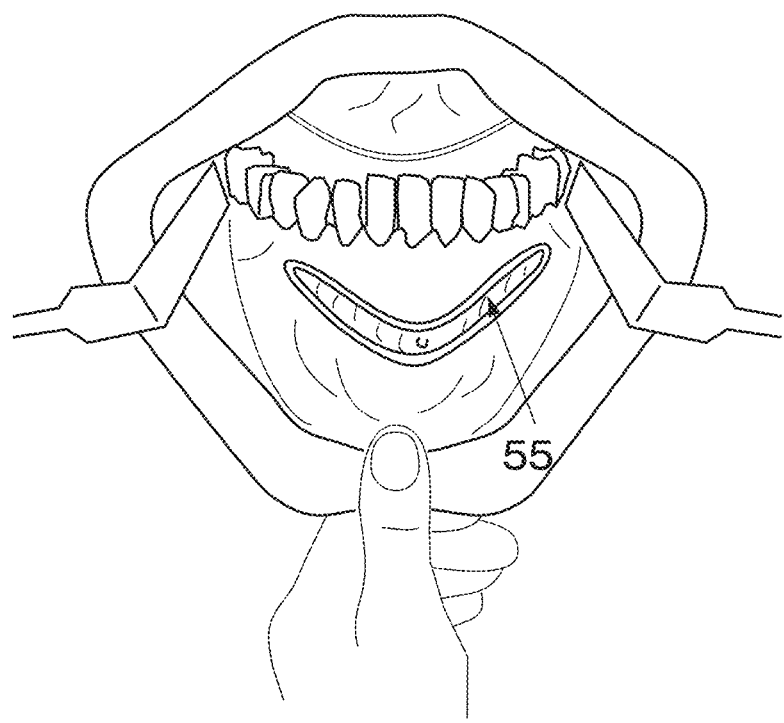
Figure 10:
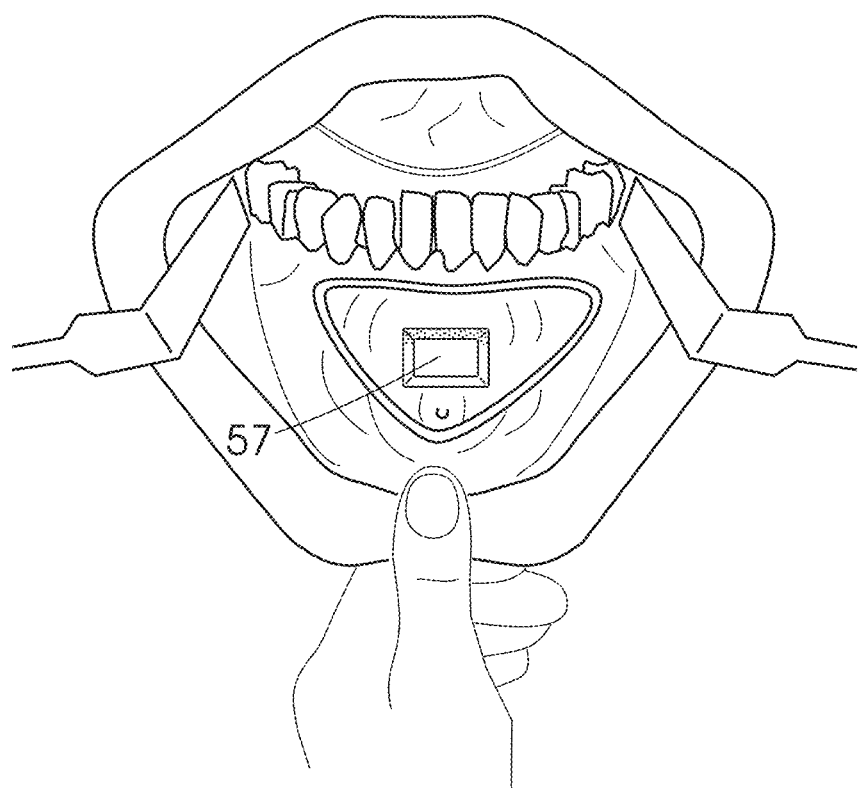
Figure 11:
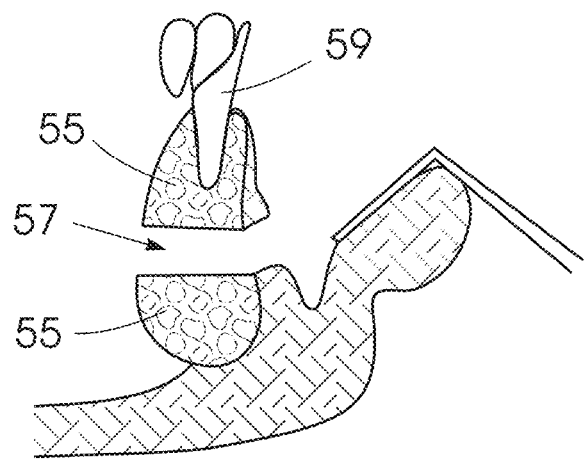

Initially the lower lip (51) is retracted and a vestibular incision (53) is carried out to incise the mucosa and Mentalis muscle of the chin as shown in FIG. 8. The Mentalis muscle is then stripped to expose the bony prominence (55) of the chin as shown in FIG. 9. A fenestration (57) or window is then formed in the prominence (55) of the chin at a subapical level of the lower incisor teeth (59) as shown in FIGS. 10 and 11. The fenestration is created by an osteotomy of both the outer and inner cortices of the bone. A 701 bur is used to make the perforation in the bone which is then removed through an osteotome. It is recommended to remove each cortex separately.

Access to the floor of the mouth is thus achieved. Alternatively, a bone trephine measuring 10 mm in diameter may also be used to create the fenestration access. FIG. 11 illustrates the bicortical fenestration (57) to the floor of the mouth as seen from a lateral perspective. It is within this fenestration bony defect that a fixation screw will be placed in order to provide anchorage to the implantable device.

Figure 12:
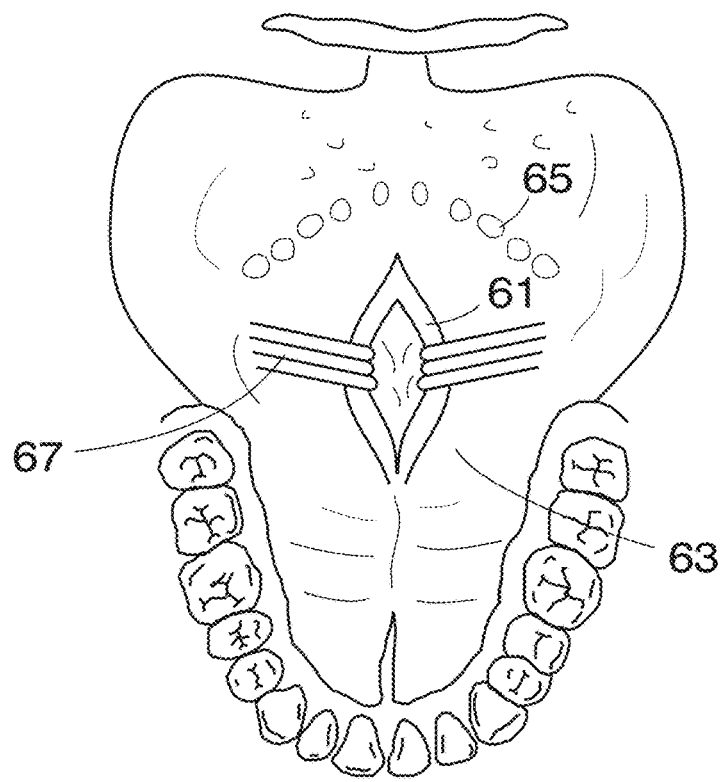
Figure 13:
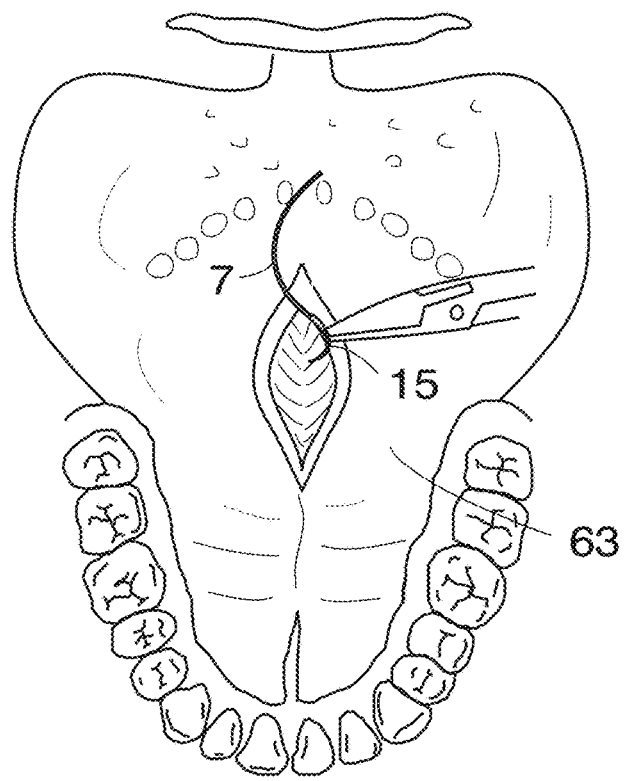
Figure 14:
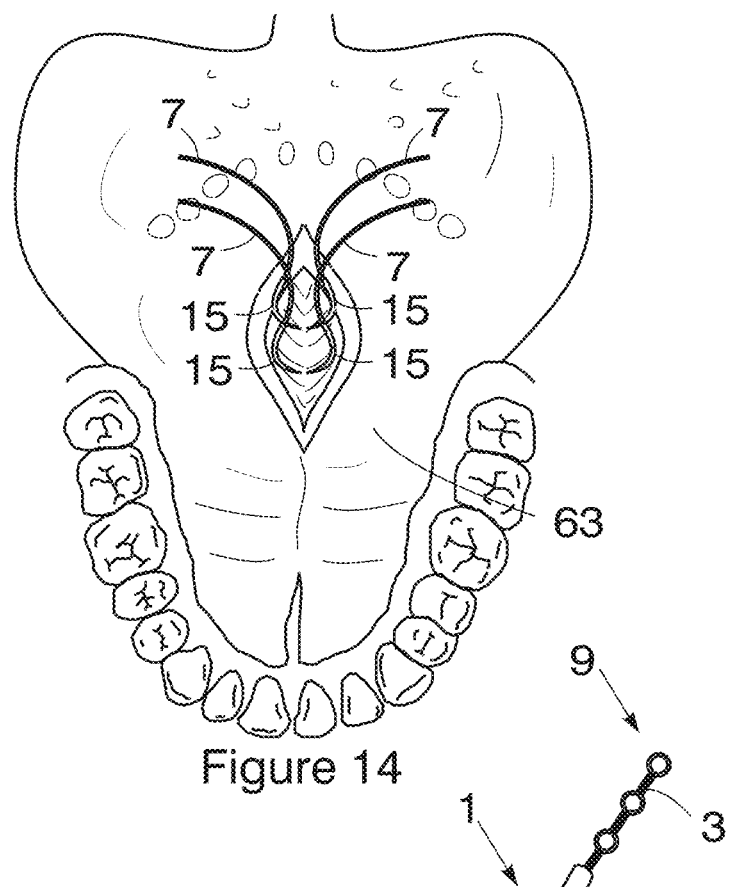
Figure 15:
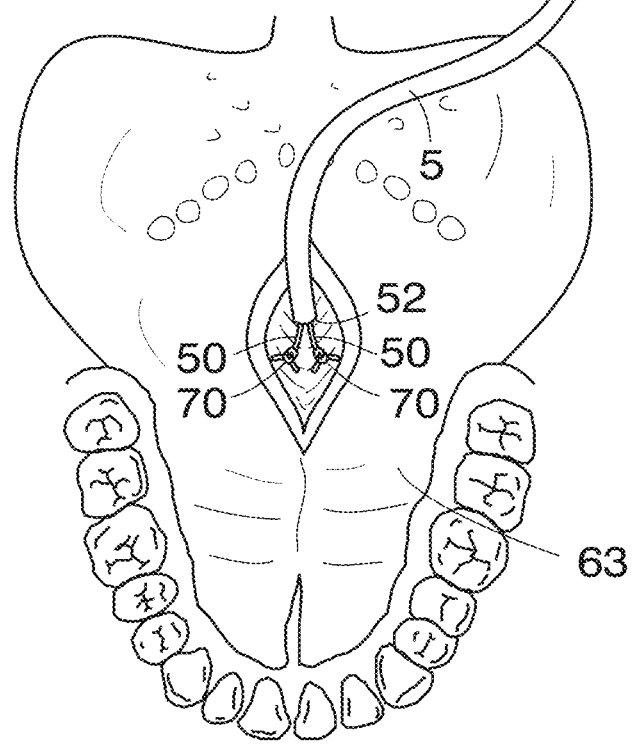

A second incision (61) is made on the dorsal aspect of the tongue (63) just anterior to the V-shape depicted by the circumvallate papillae (65) as shown in FIG. 12. Sharp dissection is carried through to the tongue base while the wound is retracted laterally using traction sutures (67). Referring to FIGS. 13 to 15, two anchorage sutures (50) are inserted deep into the intrinsic muscle of the tongue (63), one being anterior and the other posterior, using the needles (15) and filaments (7) at the end (13) of the device (1) shown in FIGS. 1 and 2. After the needles (15) have been removed and discarded, the sutures (50) are tensioned and tied together so that the two on the right side make a single knot (70) and the same is done for the two on the left side. In this way, the end (52) of the scaffold (5) is well embedded into the base of the tongue (63) as shown in FIG. 15. The knotted end of the device (1) is illustrated in the deep aspect of the tongue muscle before the push through into the floor of the mouth. By pulling anteriorly on the device (1) the validity and strength of the attachment to the tongue base is tested clinically.

The device (1) is soaked in a solution of 200 ml of saline mixed with Gentamycin™ (Fresenius 80 mg/2 ml vials) for at least 30 minutes before insertion. This precaution is to prevent infection of the device (1) and particularly the porous scaffold (5). Also, a non-touch technique, preferably avoiding contact with the facial skin should be employed.

Figures 16, 17:
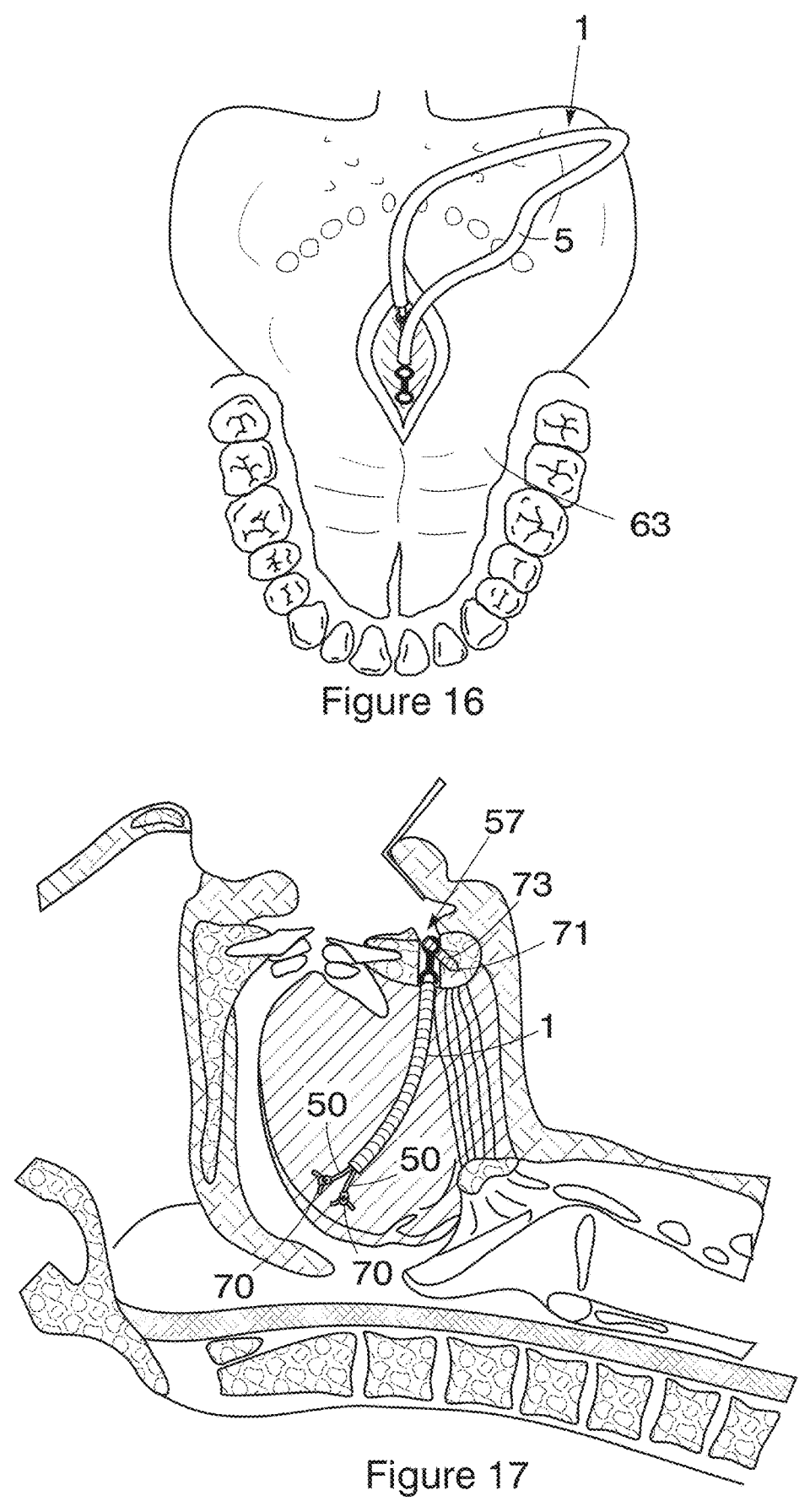

Once the validity and strength of the attachment is shown to be satisfactory, the push through/pull through method is employed. A curved, blunt artery forceps is used to engage one of the loops (17, 19, 21) and carry the first end (9) of the device (1) through the floor of the mouth towards the fenestration in the chin (FIG. 16). The first end (9) of the device (1) is then engaged through the chin fenestration and pulled through gently. The base of the tongue is then advanced towards the chin a desired distance using the tether. Advancing the base of the tongue about 10 mm is typically sufficient and is often denoted by a depression in the base of the tongue. The 10 mm spacing of the loops (17, 19, 21) simplifies the distance estimation when the tongue needs to be advanced by 10 mm.

A 9 mm by 2.0 mm hole (71) is drilled into the medulla of the chin within the fenestration window (57) and the same size Lactosorb™ screw (73) is secured in the hole (71) after being fed through an appropriate loop (17, 19, 21) in the tether (3), as shown in FIG. 17.

The bone that is removed is not replaced as new bone will eventually fill into the gap. The Lactosorb™ screw is absorbable and degrades very slowly through hydrolysis after 32 weeks and is only completely absorbed after 52 weeks. Its initial strength within the first 32 weeks more or less equals that of titanium.

The wound on the dorsum of the tongue is closed using a USP 3-0 polyglycolic acid suture and the wound in the lip is closed with USP 5-0 polyglycolic acid suture.

As shown in FIG. 17, in its final implanted position the device (1) provides a tongue support which not only supports the tongue base from falling against the posterior pharyngeal wall during sleep, but also advances the tongue base so that the compliance of the oro- and hypopharynx is improved and secured, thereby making obstruction of the lower airway AW impossible.

While the check is initially provided by the tether (3), during the time in which it takes for the PDO of the filaments (7) to be absorbed, tissue ingrowth and collagen deposition within the pores and on the scaffold (5) and between the scaffold (5) and tether (3) occurs. After absorption of the filaments (7) the device forms a naturally induced biological tendon which provides the check on the tongue and the protection that the tongue lacks anatomically. This then avoids the problems and discomfort associated with migration of the implant through the base of the tongue.

At the same time all physiological aspects of tongue muscular function, like speech, swallowing and chewing are not in any way adversely affected by the device (1). The scaffold may remain implanted, but is barely visible as a tendon has developed in and around it. In an embodiment in which the scaffold is degradable over time, it will eventually disappear and only the naturally formed tendon remains.

Thereafter the collagen undergoes maturity. This means that after the disappearance of the PDO filaments, the scaffold will be overgrown with collagen bands (including types 1 and 3 confirmed by means of electrophoresis) which will not only provide tensile strength to the neo-tendon, but is histologically and biologically attached to the intrinsic tongue muscle of the tongue through the process of orderly fibrosis, never previously described for inventions of this nature.

The collagen bands strengthen as they are continuously stressed by the movement of the tongue muscle. The movement induces further growth of the collagen bands until maturation is achieved. The more stress that is applied to the collagen bands during movement of the tongue, the more the collagen grows or accumulates and the stronger the collagen bands become. This characteristic of collagen growth and strengthening explains, for example, why the tendon of a thigh is stronger than that of finger muscles. The tendon of a thigh grows and strengthens as it experiences more stress in comparison to the tendons in a finger.

Histological studies in sheep have shown that the polyurethane scaffold successfully induces fibrovascular tissue ingrowth within the first 8 weeks post implantation.

Tests were conducted to determine the stress strain behaviour and possible differences in the ultimate strengths of explanted devices comprising the device described above (PDO+PU), a polyurethane scaffold alone (PU), polydioxanone filaments alone (PDO) and a polypropylene device (PP) in sheep. The devices were all implanted in sheep in the same manner as described. The implanted devices were explanted at 8 weeks, 16 weeks and 32 weeks respectively.

Explanted samples of week 8 were clamped using Instron grips and pulled at a rate of 5 mm per minute. Three PDO+PU samples and two PDO samples were supplied and evaluated. There were distinct differences in appearance in size and shape of the samples, the PDO+PU being much thicker due to tissue growth. All samples were pulled to break and reasonable data obtained after some difficulties using the direct clamping method.

Explanted samples of week 16 could not be successfully clamped using the direct clamp method because of tissue growth and inability to obtain enough frictional force to overcome the strength of the samples. In a new method Kevlar yarn was used to tie the sample ends to the Instron jaws using knots and hitches.

Two samples of PDO, two of PP and one of PDO+PU were tested. The speed was increased to 50 mm per min to eliminate the slippage that was observed at 5 mm. This method allows for sufficient gripping of the slippery soft tissue to achieve tensile failure.

Thirty two-week explants were tested also using the Kevlar yarn method. Three samples of PDO+PU, two samples of PU, one sample of PDO and one sample of PP were tested. Samples were tensile tested at a speed of 50 mm per min and all samples apart from the PP failed in the appropriate mode. In the case of the PP samples, they needed to be cleaned of tissue to get sufficient grip using the Instron clamps to pull to break.

Figure 18:
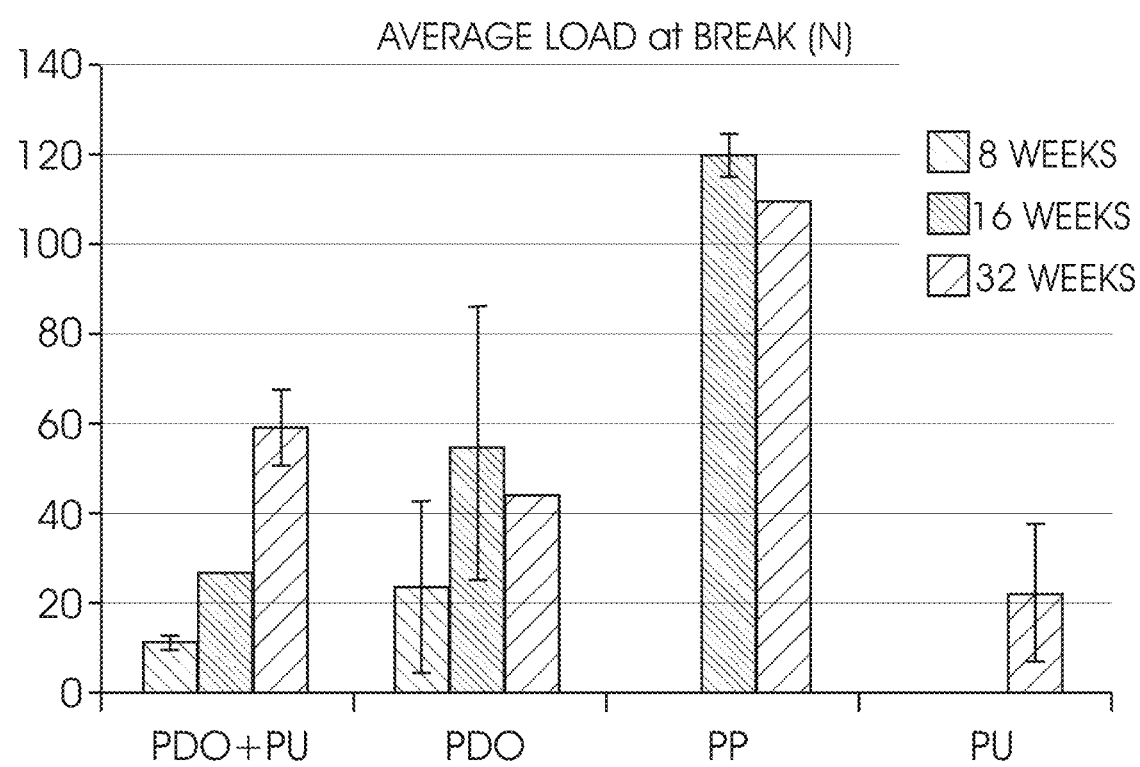
FIG. 18 is a bar graph showing the results of stress strain tests carried out on scaffolds made of polydioxanone and polyurethane (PDO+PU) and tether filaments made of polydioxanone (PDO), a polyurethane scaffold alone (PU), polydioxanone filaments alone (PDO) and a polypropylene device (PP) that were explanted from sheep after 8, 16 and 32 weeks respectively.

Results are plotted in FIG. 18 and show an increase of strength of the PDO+PU samples with increasing implant time (from 8 to 32 weeks). In the case of the PDO samples, there is also a general trend of increasing strength with time, but this is not strictly so, as one of the 16 week PDO samples was much thicker than the other, resulting in large variance and increased average ultimate tensile strength. The PP samples remained at similar strength throughout as expected due to the non-degradability of the material.

There is a clear increase in strength for the PDO+PU device with implant time. The small number of replicates and variation in explant size and shape resulted in a less clear trend with the PDO group.

The present invention is regarded as being superior to all previous implants (filamentous or metallic structures) in that the implant does not eventually rely upon a mechanical or stress interface with the intrinsic muscle of the tongue for adherence or retraction. Instead it promotes the generation of a tendon which acts as a permanent tongue check.

It will be appreciated that many other embodiments of an implantable device exist which fall within the scope of the invention, particularly regarding the shape, configuration and materials used for the tether and the scaffold. For example the scaffold could be between 50 mm and 100 mm long and be made from any suitable material. The tether too may be made from any suitable number of filaments and could be secured to the chin in any suitable manner.

It will further be appreciated that while the above described device is configured for use as a tongue support to assist in the treatment of apnoea by assisting in the formation of a tendon between the base of the tongue and the chin, the device can be configured to assist in the formation of other types of connective tissue.

Connective tissue in a mammalian body can be generated by creating an incision in the body and securing between a pair of anatomical structures which are movable relative to each other, an elongate, flexible tether carrying a scaffold such that the length of the tether is a desirable maximum distance between the anatomical structures along a desired path. The scaffold should be elongate and generally porous so as to be capable of promoting tissue ingrowth and collagen deposition along its length and it should be secured such that it is in at least close proximity to the anatomical structures at either end. The incision can then be closed and tissue ingrowth and collagen deposition permitted to take place in and on the scaffold over a period of time.

The tether should preferably be made of a material degradable within the body over a period of time. The scaffold is made of a material that is not degradable, but it foreseen that it may be desirable for the scaffold to be made of a material which is degradable within the body over a period of time.

The manner in which the tether is attached to the anatomical structures will depend on the nature of the structures and any suitable method can be used. Similarly, the shape and configuration of the tether and scaffold can be adapted to approximate the natural connective tissue it is desired to generate or to approximate desirable shape of connective tissue.

The connective tissue generated using the implantable devices of the current invention are truly biological and biologically attached to the body.

Throughout the specification unless the contents requires otherwise the word 'comprise' or variations such as 'comprises' or 'comprising' will be understood to imply the inclusion of a stated integer or group of integers but not the exclusion of any other integer or group of integers.

The invention claimed is:

1. A method of generating orderly connective tissue in a mammalian body comprising:
   creating an incision in the mammalian body; and
   securing between a pair of anatomical structures, which are movable relative to each other and disposed within the mammalian body, an elongate, flexible tether carrying a scaffold such that a length of the tether is a maximum distance between the anatomical structures along a path,
   wherein the scaffold is:
      elongate and generally porous so as to be capable of promoting tissue ingrowth and collagen deposition along a length of the scaffold, and
      secured such that the scaffold is in at least close proximity to the anatomical structures at either end of the scaffold, thereby permitting tissue ingrowth and collagen deposition in and on the scaffold over a period of time.

2. The method of claim 1, wherein the scaffold comprises pores that extend through the scaffold.

3. The method of claim 2, wherein the pores each have a diameter in a range of about 10 μm to 200 μm.

4. The method of claim 1, wherein the tether is made of a material which is absorbed into the mammalian body over a period of time.

5. The method of claim 1, wherein the scaffold is made of a material which is absorbed into the mammalian body over a period of time.

6. The method of claim 1, wherein the scaffold is carried as a sleeve over the tether.

7. The method of claim 6, wherein the sleeve is about 0.5 mm thick and has an internal diameter of about 2 mm.

8. A method of providing a support for a base of a tongue comprising:
   causing orderly connective tissue to be generated between the base of the tongue and a chin by securing between the base of the tongue and the chin an elongate, flexible tether carrying an elongate sleeve-like scaffold which is porous so as to be capable of promoting tissue ingrowth and collagen deposition along a length of the scaffold;
   advancing the base of the tongue towards the chin a distance using the tether; and
   permitting a tendon to be formed between the chin and the tongue in and on the scaffold, wherein the tether is absorbed and replaced by the orderly connective tissue, and wherein the orderly connective tissue comprises a plurality of collagen bands formed as the scaffold degrades over a period of time.

9. The method of claim 8, wherein the tether has a tensile strength of at least 20 N so as to advance the base of the tongue towards the chin and maintain the base of the tongue in a position proximate the chin.

10. The method of claim 8, further comprising stitching the tether to the base of the tongue.

11. The method of claim 8, further comprising providing one or more holes and screws for screwing the tether into the chin.

12. A method of treating sleep apnoea comprising:
securing between a base of a tongue and a chin an elongate, flexible tether carrying an elongate scaffold which is porous so as to promote tissue ingrowth and collagen deposition along a length of the scaffold;
advancing the base of the tongue towards the chin a distance using the tether; and
permitting a tendon to be formed between the chin and the tongue in and on the scaffold, wherein the tether is absorbed and replaced by orderly connective tissue, wherein the orderly connective tissue comprises a plurality of collagen bands formed as the scaffold degrades over a period of time.

13. The method of claim 12, wherein the tether has a tensile strength of at least 20 N so as to advance the base of the tongue towards the chin and maintain the base of the tongue in a position proximate the chin.

* * * * *